(12) United States Patent
Mizutani et al.

(10) Patent No.: US 7,195,620 B2
(45) Date of Patent: Mar. 27, 2007

(54) INTERLABIAL PAD

(75) Inventors: Satoshi Mizutani, Kagawa (JP); Wataru Yoshimasa, Kagawa (JP); Yuki Noda, Kagawa (JP)

(73) Assignee: Uni-Charm Corporation, Ehime-Ken (JP)

( * ) Notice: Subject to any disclaimer, the term of this patent is extended or adjusted under 35 U.S.C. 154(b) by 0 days.

(21) Appl. No.: 11/007,810

(22) Filed: Dec. 8, 2004

(65) Prior Publication Data

US 2005/0137562 A1 Jun. 23, 2005

(30) Foreign Application Priority Data

Dec. 9, 2003 (JP) ............... 2003-411085

(51) Int. Cl.
*A61F 13/20* (2006.01)
*D04H 3/00* (2006.01)

(52) U.S. Cl. ............ 604/385.17; 604/384; 428/902; 442/340; 442/414

(58) Field of Classification Search ........... 604/385.17, 604/384, 377; 428/903, 902; 442/340, 414
See application file for complete search history.

(56) References Cited

U.S. PATENT DOCUMENTS

| | | | | |
|---|---|---|---|---|
| 4,046,147 A | * | 9/1977 | Berg | 604/385.201 |
| 4,175,561 A | * | 11/1979 | Hirschman | 604/385.17 |
| 4,418,524 A | * | 12/1983 | Ito et al. | 57/239 |
| 4,595,392 A | * | 6/1986 | Johnson et al. | 604/385.17 |
| 4,673,403 A | * | 6/1987 | Lassen et al. | 604/385.17 |
| 4,773,903 A | * | 9/1988 | Weisman et al. | 604/368 |
| 4,923,454 A | * | 5/1990 | Seymour et al. | 604/368 |
| 5,019,073 A | * | 5/1991 | Roessler et al. | 604/391 |
| 5,127,911 A | * | 7/1992 | Baharav | 604/385.23 |
| 5,176,952 A | * | 1/1993 | Joseph et al. | 442/340 |
| 5,197,959 A | * | 3/1993 | Buell | 604/385.23 |
| 5,399,423 A | * | 3/1995 | McCullough et al. | 442/345 |
| 5,672,165 A | * | 9/1997 | Belecky et al. | 604/383 |
| 5,964,689 A | * | 10/1999 | McFall et al. | 493/395 |

(Continued)

FOREIGN PATENT DOCUMENTS

JP    2001-507597 A    6/2001

(Continued)

OTHER PUBLICATIONS

Abstract of WO 98/29078 (JP 2001-507597) published on Jul. 9, 1998.

*Primary Examiner*—Tatyana Zalukaeva
*Assistant Examiner*—Paula L. Craig
(74) *Attorney, Agent, or Firm*—Darby & Darby

(57) ABSTRACT

An object of the present invention is to provide an interlabial pad, with which a wearer will hardly feel a sensation of using the interlabial pad, even when a wearer moves and pressure from the exterior is applied to the interlabial pad. An interlabial pad 10, with which a wearer will hardly feel a sensation of using the interlabial pad, can be provided by equipping a crease-spanning region 2 of the interlabial pad 10 with a pressure dispersion means 11, which, in repulsion to pressures that are applied from the vestibular floor to the crease-spanning region 2 of the interlabial pad 10 in accompaniment to movements of the wearer, prevents the direct transmission of the pressures to the vestibular floor.

5 Claims, 9 Drawing Sheets

U.S. PATENT DOCUMENTS

| | | | |
|---|---|---|---|
| 6,010,001 A * | 1/2000 | Osborn, III ................. 206/440 |
| 6,131,736 A * | 10/2000 | Farris et al. ................. 206/440 |
| 6,503,233 B1 * | 1/2003 | Chen et al. ............ 604/385.01 |
| 6,923,795 B1 * | 8/2005 | Cantley et al. ......... 604/385.17 |
| 2001/0000796 A1 * | 5/2001 | Osborn et al. .......... 604/385.17 |
| 2002/0115976 A1 * | 8/2002 | Fleming ................ 604/385.17 |
| 2003/0171053 A1 * | 9/2003 | Sanders ...................... 442/340 |
| 2004/0147893 A1 * | 7/2004 | Mizutani et al. ........ 604/385.17 |
| 2004/0147894 A1 * | 7/2004 | Mizutani et al. ........ 604/385.17 |
| 2004/0147897 A1 * | 7/2004 | Mizutani et al. ........ 604/385.17 |
| 2004/0167491 A1 * | 8/2004 | Mizutani ................ 604/385.17 |
| 2004/0181201 A1 * | 9/2004 | Mizutani et al. ........ 604/385.17 |
| 2004/0199134 A1 * | 10/2004 | Mizutani et al. ............. 604/367 |
| 2005/0147810 A1 * | 7/2005 | Suzuki et al. .............. 428/339 |

FOREIGN PATENT DOCUMENTS

| | | |
|---|---|---|
| WO | WO-02/094152 A1 | 11/2002 |
| WO | WO-02/094153 A1 | 11/2002 |
| WO | WO-02/094159 A1 | 11/2002 |
| WO | WO-02/100315 A1 | 12/2002 |

* cited by examiner

INTERLABIAL PAD

CROSS-REFERENCE TO RELATED APPLICATIONS

This application is based upon and claims the benefit of priority from Japanese Patent application No. 2003-411085 filed on Dec. 9, 2003, the entire contents of which is incorporated herein by reference.

1. Field of the Invention

The present invention concerns an interlabial pad, with which a wearer will hardly feel a sensation of using the interlabial pad even when pressure is given to the interlabial pad from the exterior as a wearer moves.

2. Related Art

Conventionally, sanitary napkins and tampons have been used in general as sanitary articles for women. Sanitary articles called interlabial pads have come to be noted in recent years as a sanitary article positioned between sanitary napkins and tampons. An interlabial pad is fitted on by being sandwiched between a woman's labia and being put in contact with the inner walls of the labia, and, in comparison to a sanitary napkin, the leakage of menstrual blood is prevented due to the highly close contact with the body, and since the dispersion of menstrual blood is prevented, sanitation and cleanliness are secured. Also, since an interlabial pad is more compact than a sanitary napkin, it is excellent in fitting comfort, and also has the characteristic of being low in psychological reluctance during fitting in comparison to a tampon, which is inserted inside the vagina.

As interlabial pads with such characteristics, those with various structures have been developed. For example, the interlabial pad disclosed in Patent Document 1 is folded in two along a crease extending along a longitudinal central axis of the interlabial pad so that a back face side faces itself, and the back face side is joined to itself at least at one joined part. This interlabial pad has a structure wherein a wearer can insert a finger in the space that is formed by the joining of the back face side with itself and can thereby fit the interlabial pad in a space between the labia. An interlabial pad of such a type that is used upon being folded in two is fitted on so that the bent part that is formed by the folding in two contacts the vestibular floor, and this structure can be said to be favorable in having the merits of being readily sandwiched between the labia, fitting inside the labia, and thereby being low in the possibility of leakage of menstrual blood.

[Patent Document 1] International Patent Publication No. WO02/100315 Pamphlet

However, with the interlabial pad disclosed in Patent Document 1, the bent part and the joined part are positioned along a substantially vertical line during fitting. Thus when a wearer moves, such as sitting down on a chair and the like, a pressure is applied from the exterior to the interlabial pad that is sandwiched between the labia, since the pressure is applied directly to the bent part and presses the vestibular floor that is contact with the bent part, a wearer is made to strongly feel a sensation of using the interlabial pad.

Thus a theme of those concerned with the art was to develop an interlabial pad, of a type that is folded in two, with which a wearer will not feel the sensation of using the interlabial pad even when pressures are applied to the interlabial pad from the exterior. The present invention has been made in view of this theme, and an object thereof is to provide an interlabial pad, even when pressure applied from the exterior as a wearer moves, the wearer will hardly feel the sensation of using the interlabial pad.

SUMMARY OF THE INVENTION

The present inventors carried out diligent research concerning how to provide an interlabial pad, of a type that is folded in two, with which, even when pressure applied from the exterior as a wearer moves, the wearer will not strongly feel the sensation of using the interlabial pad. As a result, the inventors found that by equipping an interlabial pad with a pressure dispersion means, which disperses pressures that are applied from the vestibular floor to the interlabial pad when a wearer moves, an interlabial pad can be provided with which a wearer will hardly feel the sensation of using the interlabial pad. Specifically, the present invention provides the following:

(1) An interlabial pad, comprising, in a fitted state: a body side face facing a body side; and an opposite body side face facing the side opposite to the body side face; and being formed to a practically longitudinal shape having a longitudinal direction and a lateral direction; wherein the interlabial pad is fitted by being folded in two so that the opposite body side face faces itself in the lateral direction, and held between the labia in a state in which at least a part of a portion along a crease as a folding axis formed by being folded in two contacts the vestibular floor in the labia; and wherein the interlabial pad is equipped, at a crease-spanning region, with a pressure dispersion means which, in response to a pressure that is applied to the interlabial pad when a wearer moves, prevents the pressure from being directly transmitted to the vestibular floor.

The interlabial pad according to (1) is a folded-in-two type interlabial pad which is provided with a pressure dispersion means at a region spanning a crease for folding the interlabial pad, so that the pressure dispersion means can disperse a pressure that arises when the vestibular floor strongly presses the crease-spanning region of the interlabial pad in accompaniment to movements of a wearer. Here, "vestibular floor" refers to the base part of the left and right labia, that is, a region extremely sensitive to stimuli applied from the exterior which is positioned at the interior of the labia along a line joining the clitoris and the ostium vaginae. Also, "crease-spanning region" refers to a region that includes the crease, which is the folding axis for folding the interlabial pad in two, and is positioned along the crease, and at least a part thereof contacts the vestibular floor during fitting of the interlabial pad. In the present Specification, the "pressure dispersion means" is a means by which, when a wearer sits on a chair, etc., and the vestibular floor strongly presses the crease-spanning region, the crease-spanning region expands and deforms so as to disperse the pressure in outward directions that intersect the direction of the pressure (see FIGS. 1, 2, and 3).

In a conventional folded-in-two type interlabial pad, when a strong pressure is applied to the crease-spanning region from the vestibular floor, both side parts of the fold, which are formed at both sides of the crease by folding the interlabial pad in two deform by buckling and such, before the crease-spanning region deforms. This is because, by folding the interlabial pad in two, the bending strength of the crease-spanning region is increased. Thus in the conventional folded-in-two type interlabial pad, the wearer is made to feel the sensation of using the interlabial pad due to the crease-spanning region not deforming, and in addition, since the side parts of the fold deform, close contact with the inner labial walls is lost and the possibility of leakage of menstrual blood is increased.

In regard to this point, with the interlabial pad of (1), since a pressure dispersion means is provided so as to span the crease, pressures that are applied from the vestibular floor to the crease-spanning region can be dispersed in outward directions and the vestibular floor will therefore not receive a strong repulsive force from the interlabial pad. To be more specific, when a wearer moves and the vestibular floor strongly presses the crease-spanning region, since the crease-spanning region expands and deforms so as to disperse the pressure in outward directions that intersect the direction of the pressure, the interlabial pad will be unlikely to press the vestibular floor in repulsion to the pressure and the wearer will hardly feel the sensation of using the interlabial pad. Thus with the interlabial pad of (1), even when the wearer moves and pressures from the exterior arises, the wearer can go about with daily life comfortably without feeling the sensation of using the interlabial pad.

With the interlabial pad of (1), the pressure dispersion means is provided so as to span across the crease, and this includes cases where there is a space between the pressure dispersion means and the crease (see, for example, FIG. 15), and there are no restrictions in particular as long as the pressure dispersion means is positioned so as to span the crease. Though the pressure dispersion means may be positioned at the entirety of the interlabial pad, it is preferably provided in a region that contacts the clitoris and the ostium vaginae, which are sensitive to stimuli. Also, though the crease is preferably provided along a central axis in the longitudinal direction, the crease as referred to by the present invention includes all creases that are formed by folding in two. The folded-in-two type interlabial pad as referred to by the present invention includes both that which is folded in two from the beginning and that which is folded in two in the fitting process.

Though as mentioned above, the crease-spanning region refers to the region that includes the crease which is the folding axis for folding the interlabial pad in two, and the region along the crease, the length in the lateral direction thereof is preferably in a range from 0.5 mm to 40 mm and more preferably in a range from 5 mm to 20 mm. Also, though the crease may be straight line directed in the longitudinal direction, it is preferably of a zigzag shape, wavy shape, or other shape with an apparent width in that the crease-spanning region will then expand further and deform more readily.

Furthermore, in order to effectively prevent the outflow of menstrual blood or fall-off of the interlabial pad and such, in addition to providing the abovementioned effects, the external dimensions of the interlabial pad of (1) are preferably such that the total length in the longitudinal direction is in a range from 50 mm to 180 mm and more preferably such that the above-mentioned length is in a range from 80 mm to 120 mm in consideration of the external shape of the labia and the size of the space that is formed between the labia and shorts. Also, the total width of each of the side parts of the fold at both sides of the crease is preferably in a range from 15 mm to 50 mm and more preferably in a range from 25 mm to 40 mm.

The interlabial pad of (1) may be equipped with a liquid-permeable surface side sheet which is positioned at the body side face, an absorbent which absorbs and holds body fluids, and a liquid-impermeable back face side sheet which is positioned at the opposite body side face. In this case, a sheet that is liquid permeable and does not readily irritate the skin is generally used as the surface side sheet. For example, fibers selected from among those having a fiber length in a range from 5 mm to 51 mm and more preferably in a range from 25 mm to 51 mm and having a Young's modulus preferably in a range from 100 kg/mm$^2$ to 1500 kg/mm$^2$ and more preferably in a range from 300 kg/mm$^2$ to 1000 kg/mm$^2$, are used. For example, rayon, acetate rayon, natural cotton, pulp, chemical pulp, or fibers being formed solitarily of a synthetic resin component or being formed as a composite having core-sheath structure of synthetic resin components, may be used in solitary or mixed form. These fibers may differ in cross-sectional shapes, which may be Y-like or C-like, or may be crimped fibers or fibers that have been made high in molecular orientation by a drawing process.

Such fibers are layered at the crease-spanning region and thereafter formed into a sheet by spun bonding, point bonding, air through method, needle punching, dry- or wet-form spun lacing, or other method to form the surface side sheet. Specifically, a spun-lace non-woven fabric, prepared by mixing 5 to 30% natural cotton with 70 to 95% rayon or acetate rayon, adjusting the basis weight per unit area of the mixed fibers to within a range from 20 to 50 g/m$^2$, entangling the fibers with each other by hydroentanglement, and then drying and adjusting the thickness to within a range from 0.3 to 1.0 mm, is used. In regard to the fiver quality to be used, natural cotton of a fiber length in a range from 15 to 60 mm and rayon or acetate rayon of a fiber length in a range from 25 to 51 mm and a fineness in a range from 1.1 to 6.6 dtex are selected.

Also, in case that the interlabial pad is folded in two and the thickness of the absorbent at the crease-spanning region becomes thinner than the thickness of the absorbent at the side parts of the fold, the crease-spanning region will not deform readily when a pressure is applied from the vestibular floor to the crease-spanning region. In order to prevent this, it is effective to use a surface side sheet that can extend readily in the lateral direction, and the thinning of the thickness of the absorbent at the crease-spanning region can thereby be prevented.

As examples for forming a surface side sheet that can extend readily in the lateral direction, a method for increasing the ductility among the respective fibers that form the surface side sheet can be cited. As examples of fibers necessary for forming such a surface side sheet, fibers of high crimp percentage, fibers having been improved in extensibility by the mixing in of a rubber component, split fibers, fibers of low molecular orientation and such, can be cited. For increasing the ductility among the respective fibers, the use of fibers having a lubricant mixed therein, the use of fibers with which fibers of Y-like cross section, fibers of C-like cross section and such are mixed to reduce the area of contact of fibers with each other and such can be cited. Another method of providing extensibility of the surface side sheet in the lateral direction, the method of applying wave-like engagement embossing in the lateral direction can be cited, and with this method, the extensibility can be controlled by the size and pitch of the wave-like forms. Here, "extensibility" refers to the amount by which the original length in the lateral direction of the surface side sheet extends due to the forming of the wave-like forms (for example, if the original length in the lateral direction of the surface side sheet is 100 mm, and this length becomes 200 mm by the forming of wave-like forms, the extensibility is 2 times). Specifically, by providing an engagement pattern with a height of 1.12 mm and a pitch of 2 mm, the extensibility is made 1.5 times. As another example, the total length in the lateral direction of the surface side sheet is made longer than the total length in the lateral direction of the back face side sheet and a sagging part of the surface side sheet is set at the crease-spanning region. Since the surface side sheet can thus extend readily in the lateral direction due to the sagging part when the sheet is folded in two, the thinning of the thickness of the absorbent at the crease-spanning region can be prevented.

The surface side sheet is not restricted to a fiber aggregate formed by aggregating the above-mentioned fibers and may instead be an open pore film. In the case of an open pore film, it is preferable that, in the crease-spanning region, the open pore diameter is in a range from 0.2 mm to 5 mm, the pitch is in a range from 0.2 mm to 10 mm, and the open pore area percentage is in a range from 10% to 50%, and preferable that, in parts besides the crease-spanning region, the open pore diameter is in a range from 0.05 mm to 3 mm, the pitch is in a range from 0.2 mm to 10 mm, and the open pore area percentage is in a range from 3% to 30%. With regard to the method of manufacture, a so-called PFW may be formed by passing a film through a patterned ram with varied pore-opening conditions and then opening pores by applying suction to the film, or open pores may be added further by performing pin embossing on the crease-spanning region of a surface side sheet with uniform open pore conditions that has been obtained by the PFW method. The alignment of the open pores may be staggered, lattice-like, wave-like and such, and is not restricted in particular. Also, the pore shape may be circular, elliptical, rectangular and such. Valves may also be formed in the peripheries of the open pore parts. Preferably, in order to make it difficult for the open pores to become closed by the valves even when an external pressure is applied, the height of the valves of the open pore parts of the crease-spanning region in particular is made lower than the height of the valves in regions besides the crease-spanning region.

Also, a fiber aggregate may be used as the absorbent. For example, fibers selected from among those with a fiber length in a range preferably from 5 mm to 51 mm and more preferably in a range from 25 mm and no more than 51 mm and a Young's modulus preferably in a range from 100 kg/mm$^2$ to 1500 kg/mm$^2$ and more preferably in a range from 300 kg/mm$^2$ to 1000 kg/mm$^2$, are used. As examples, rayon, acetate rayon, natural cotton, pulp, chemical pulp, polymer absorbent body, fibrous polymer absorbent body, or synthetic fibers and such, may be used in solitary form or as a mixture and the fibers are preferably bulky, lasting in form, and low in chemical irritability. These fibers may differ in cross-sectional shapes, which may be Y-like or C-like, or may be crimped fibers or fibers that have been made high in molecular orientation by a drawing process.

As a specific example, a non-woven fabric sheet, having a basis weight per unit are of not less than 50 g/m$^2$ and not more than 500 g/m$^2$ and a bulk of not less than 1 mm and not more than 20 mm and being formed by mixing and layering fibers of not more than 60% and not less than 95% rayon or acetate rayon, selected from among those with a fineness in the range of not less than 1.1 dtex and not more than 6.6 dtex, with not less than 5% and not more than 40% natural cotton and forming a sheet by embossing, can be cited. Also, a sheet, formed by layering the abovementioned fibers at the crease-spanning region and performing the air laid method, melt blown method, spun lacing method, or papermaking method, etc., may be embossed by needling or passing between rolls of dot-form, lattice-form, etc. The embossed area percentage is preferably in a range from 0.3% to 60%. As yet another specific example, an arrangement can be cited wherein pulp of a fiber length of not more than 8 mm is layered to 100 g/m$^2$ at a part of the absorbent at regions that do not span the crease and a mixture of 85% rayon of 3.3 dtex and a fiber length of 51 mm with 15% natural cotton is layered to 180 g/m$^2$ over the entire absorbent surface upon orienting the fibers so as to cross the crease at the absorbent at the crease-spanning region. Since when the fiber length is short, there are few mutual entanglement points of fibers, the density is high and the rigidity tends to become high, when pulp of short fiber length is used in the regions that do not span the crease, the rigidity of these regions will be higher than the rigidity of the crease-spanning region. Since the regions that do not span the crease will thus not deform readily when the vestibular floor contacts the crease-spanning region at a high pressure, the crease-spanning region will expand and deform even more readily and a strong repulsive force will not be applied to the vestibular floor.

(2) The interlabial pad according to (1), wherein the interlabial pad has a fiber aggregate equipped at the crease-spanning region, and wherein the pressure dispersion means has fibers oriented so as to cross the crease in order to control the property of repulsion against the pressure.

The crease-spanning region of the interlabial pad according to (2) is provided with fibers, which are oriented so as to cross the crease, as the pressure dispersion means. Thus even when the interlabial pad of (2) is folded in two, the respective fibers that are provided at the crease-spanning region have a repulsive rigidity that make them tend to return to their original shapes. Thus when a wearer sits on a chair and such, and the vestibular floor presses the crease-spanning region with a strong pressure, the crease-spanning region, which has repulsive rigidity, can expand and deform readily and disperse the pressure in outward directions that intersect the direction of the pressure. The interlabial pad will therefore hardly press the vestibular floor in repulsion to the pressure and the wearer can go about with daily life comfortably while hardly feeling the sensation of using the interlabial pad.

In the interlabial pad of (2), among the fibers of the fiber aggregate forming the interlabial pad, at least a part of the fibers forming the members that are positioned at the crease-spanning region are oriented so as to intersect the crease. Here, "fiber aggregate which has fibers oriented so as to intersect the crease" refers to a fiber aggregate wherein the fibers orientate to form an angle with respect to the crease and the fiber orientations are at least not parallel to the crease. Also, it is sufficient that at least a part of the fibers forming the respective members that are positioned at the crease-spanning region are oriented so as to intersect the crease.

As the fiber aggregate forming the interlabial pad of (2), for example, a liquid-permeable surface side sheet formed of a fiber aggregate, an absorbent mainly formed of a fiber aggregate and absorbing and holding body fluids, etc., can be cited. Only the fibers of the surface side sheet that is formed of the fiber aggregate may be oriented so as to intersect the crease, or only the fibers of the absorbent that is formed of the fiber aggregate may be oriented so as to intersect the crease. Or the fibers of both of these fiber aggregates may be oriented so as to intersect the crease. Furthermore, in such a case where each of the surface side sheet and the absorbent has a multi-layer structure, it is sufficient that at least the fibers of the fiber aggregate of one of such layers be oriented so as to intersect the crease.

As an index for expressing the orientation of the fibers to intersect the crease, the ratio of the maximum tensile strength in the MD direction to maximum tensile strength in the CD direction (MD/CD ratio of the maximum tensile strength) of each of the surface side sheet and the absorbent may be used. Here, MD indicates the longitudinal direction of a fiber aggregate and CD indicates the lateral direction of a fiber aggregate. Specifically, the MD/CD ratio of the maximum tensile strength is preferably in a range from 0.1 to 7.0 and more preferably in a range from 0.5 to 2.5. Here, when the MD/CD ratio of the maximum tensile strength is 1, it means the state in which the orientation of the fibers in the MD and the orientation in the CD are substantially the same. Also for orienting the fibers so as to span the crease, a long fiber length is preferable, and specifically, the fiber length is preferably in a range from 5 mm to 51 mm and more preferably in a range from 25 mm to 51 mm.

The Young's modulus (=stress/strain) may be generally used as an index indicating the repulsive rigidity of the fibers. Specifically, the Young's modulus of the fibers is preferably in a range from $100 \text{ kg/mm}^2$ to $1500 \text{ kg/mm}^2$ and more preferably in a range from $300 \text{ kg/mm}^2$ to $1000 \text{ kg/mm}^2$. The repulsive rigidity is adjusted by changing the fineness, and specifically, a fineness in a range from 1.1 dtex to 6.6 dtex is selected.

The absorbent that is formed from the above-described fiber aggregate has elasticity in addition to the absorbent's inherent function of absorbing and holding body fluids, and when a pressure is applied, the absorbent can disperse the pressure in repulsion to the pressure. As a raw material for forming such an absorbent, a mixture of an elastic raw material and an absorbent raw material can be cited as an example, and as examples of an elastic raw material, fibers with elasticity and foamed materials having air cells can be cited. As an example of fibers with elasticity, fibers, formed of polyethylene (PE), polypropylene (PP), polyethylene terephthalate (PET) or other thermoplastic material and using such a resin in solitary form or using such resins in a core-sheath structure or side-by-side structure, can be cited. Preferably, the fibers are those that have been subject to secondary crimping mechanically or by heating, etc. In consideration of fitting comfort, the fiber thickness is preferably adjusted to be in a range from 0.5 dtex to 8.8 dtex and the fiber length is preferably adjusted to be in a range from 3 mm to 64 mm. As a foamed material, a material, obtained by foaming PE or PP, which has elasticity, or foaming urethane, rubber, or other resin of high elasticity, is used. Furthermore, a cellulose sponge, etc., which has a water absorbing property, can be used favorably. The absorbent is formed by cutting and making such a material filamentous, granular, etc., and then mixing it with an absorbent raw material. As the absorbent raw material, in addition to flap pulp, rayon, cotton, and other general raw materials, SAP (superabsorbent polymer) or other high molecular weight absorbent polymer of granular or fibrous form is used. In regard to the component ratio of the elastic raw material to the absorbent raw material, the elastic raw material to absorbent material ratio as weight ratio is preferably in a range from 1 to 4, to 4 to 1. Also, in view of the thickness and fitting comfort of the interlabial pad, the basis weight per unit area of the absorbent is preferably in a range from $20 \text{ g/m}^2$ to $500 \text{ g/m}^2$ and more preferably in a range from $50 \text{ g/m}^2$ to $400 \text{ g/m}^2$.

Also, the above-described absorbent may have rigidity in addition to elasticity. Here, "rigidity" refers to the resistance against deformation of an object when a force that tends to deform the object is applied to the object from the exterior. That is, as long as the crease-spanning region can be provided with elasticity, a rigid raw material may be used besides an elastic raw material in the absorbent at the crease-spanning region as well. A rigid raw material may also be used in the absorbent at the respective side parts of the fold as well. This is preferable since in this case, when a pressure is applied to the crease-spanning region from the vestibular floor, the respective side parts of the fold, which have a rigid raw material, do not deform readily and the crease-spanning region will thus expand and deform more readily.

Rigidity can also be provided by increasing the basis weight per unit area and/or increasing the thickness of the absorbent. Specifically, the basis weight per unit are of the absorbent with rigidity is preferably made at least 20% higher than that of an absorbent without rigidity. As methods of increasing the basis weight per unit are, in addition to the method of increasing the amount of the absorbent raw material, the method of making the depth of the pattern plate used in the absorbent layering process deeper, the method of increasing the layering amount by making suction stronger, the method of overlapping a second absorbent at parts, etc., can be cited. Specifically as a method of increasing the density of the absorbent, the method of embossing the absorbent at the crease-spanning region of the interlabial pad that has been folded in two can be cited. However, it is not preferable for the proportion occupied by an absorbent that has been made thin in thickness by embossing to become too high since the interlabial pad will tend to fall off and the rigidity will become too high and lower the fitting comfort. In regard to the embossing process, an absorbent, in which a part of the absorbent is embossed, can be obtained by preparing a roll having an emboss pattern formed on a base material of metal or rubber, etc., and a roll having a flat or engagement pattern, and passing the absorbent between the two rolls. The rigidity can also be adjusted in this process by adjusting the temperature and pressure appropriately. In regard to the emboss pattern, in addition to flatly compressing types of embossing, embossing types of compressing in intermittent patterns of rectangles or circles, intermittent embossing types in which an emboss pattern of high compression and an emboss pattern of intermediate compression are formed alternately, etc., can be cited. The absorbent can also be provided with rigidity by adding an adhesive agent to the absorbent. As the absorbent, a generally-used rubber-based, olefin-based, or other type of HM (hot melt adhesive agent) is used without any restrictions in particular, and such an HM is melted and applied to the surface or interior of the absorbent. As non-contacting methods of coating, coating by spraying, spiral application, beating, CC, curtain coater, Durer weaving, etc., can be cited and as contacting methods of coating, coating by coater, roll coater, etc., can be cited. Besides an HM, a water-soluble paste, etc., may also be used.

Also, a sheet member, which has elasticity and is a member that differs from the absorbent, surface side sheet, and back face side sheet, may be provided at the crease-spanning region. The position of this sheet member is not restricted in particular as long as it is in the crease-spanning region and, for example, in the case of an interlabial pad having a liquid-permeable surface side sheet at the body side face, a liquid impermeable back face side sheet at the side face opposite the body side, and an absorbent, positioned between these sheets, the abovementioned sheet member may be positioned between the back face side sheet and the absorbent or positioned between the surface side sheet and the absorbent or sandwiched in the absorbent, etc. As this sheet member, a non-woven fabric using an abovementioned elastic raw material is used favorably. As a method of manufacturing the non-woven fabric, the method of layering fibers using a card, bonding the fibers by melting the thermoplastic fibers, and thereafter forming by the through air method can be cited, and a non-woven fabric that is obtained by this method is favorable in having a repulsive elastic property. Besides this, a fabric formed by the generally-used method of point bonding, spun bonding, Water Jet, (WJ) or a spun bonding method, wherein a continuous filament is spun and bonded by hot embossing, or an SMS sheet (three layered sheet of spun bond/melt blown/spun bond), formed by blowing a melt onto a spun bonded fabric and then performing bonding, etc., may be used. Furthermore, a chemical bonding method, wherein a binder is coated onto the surface after the layering of fibers to perform bonding, or an air laid method may also be used.

(3) The interlabial pad according to (1) or (2), wherein the pressure dispersion means has a slit formed at the crease-spanning region.

In the crease-spanning region of the interlabial pad according to (3), slitting is applied as the pressure dispersion means. By applying slitting to the crease-spanning region like this, the crease-spanning region can be provided with repulsive rigidity. Thus with the interlabial pad of (3), when a wearer sits on a chair and such, and the vestibular floor presses the crease-spanning region with a strong pressure, the crease-spanning region, which has repulsive rigidity, can expand and deform readily and disperse the pressure in outward directions that intersect the direction of the pressure. The interlabial pad will therefore hardly press the vestibular floor in repulsion to the pressure and the wearer can go about with daily life comfortably while hardly feeling the sensation of using the interlabial pad.

In regard to the slitting, the slits preferably have a dimension in a range from 1 mm to 20 mm and are of a pitch in a range of not more than 20 mm, and the slit pattern may be of the longitudinal direction, lateral direction, diagonal direction, a combination of such directions, or may be intersecting. The shape of the slits is not restricted in particular and may be linear, curved, wave-like, etc. The slits may be made so as to pass through in the thickness direction or so as not to pass through in the thickness direction. Furthermore, it is preferable to provides another slits in a direction orthogonal to the abovementioned slits, since in this case, when the vestibular floor presses the crease-spanning region with a strong pressure, the crease-spanning region will expand and deform so as to disperse the pressure in multiple directions, and a wearer will thereby made extremely unlikely to feel the sensation of being fitted with the interlabial pad.

(4) The interlabial pad according to (1) or (2), wherein the pressure dispersion means has an embossing pattern formed at the crease-spanning region.

In the crease-spanning region of the interlabial pad according to (4), embossing is applied as the pressure dispersion means. By applying embossing to the crease-spanning region like this, the crease-spanning region can be provided with repulsive rigidity. Thus with the interlabial pad of (4), when a wearer sits on a chair and such, and the vestibular floor presses the crease-spanning region with a strong pressure, the crease-spanning region, which has repulsive rigidity, can expand and deform readily and disperse the pressure in outward directions that intersect the direction of the pressure. The interlabial pad will therefore hardly press the vestibular floor in repulsion to the pressure and the wearer can go about with daily life comfortably while hardly feeling the sensation of using the interlabial pad.

The embossing pattern is not restricted in particular and may be of the dot-form, line-form, wave-form, lattice-form, and such. Dot-form embosses may be formed in plurality at a pitch in a range from 5 mm to 20 mm in the crease-spanning region, or line-form embosses of dimensions of not less than 5 mm and not more than 20 mm may be formed in plurality in a direction substantially orthogonal to the crease at a pitch in a range from 5 mm to 20 mm in the crease-spanning region. Such slit or embossing pattern may be applied not only to the absorbent body but may also be applied to the surface side sheet and the back face side sheet.

(5) The interlabial pad according to (1), wherein the interlabial pad is equipped with a liquid-impermeable, elastic sheet at the opposite body side face, and wherein the pressure dispersion means is provided in the elastic sheet.

The interlabial pad according to (5) is equipped with a liquid-impermeable elastic sheet that is provided with the pressure dispersion means, and the elastic sheet is disposed so as to span the crease. Here, "elastic" refers to an object's property of deforming when a force is applied to the object from the exterior and then returning immediately to the original form when the force is removed. That is, the elastic sheet provided in the interlabial pad according to (5) has the property of deforming and restoring in form readily. Thus with the interlabial pad according to (5), when a wearer sits on a chair and such, and the vestibular floor presses the crease-spanning region with a strong pressure, the crease-spanning region, which has repulsive rigidity, can expand and deform readily and disperse the pressure in outward directions that intersect the direction of the pressure. The interlabial pad will therefore hardly press the vestibular floor in repulsion to the pressure and the wearer can go about with daily life comfortably while hardly feeling the sensation of using the interlabial pad.

As methods of providing the elastic sheet with elasticity, methods of using an elastic raw material can be cited. By using an elastic raw material in the elastic sheet, when a pressure is applied from the vestibular floor to the crease-spanning region, the crease-spanning region can be made to expand and deform readily and disperse the pressure in outward directions that intersect the direction of the pressure. As the elastic raw material, a laminate or film of fibers with elasticity or a foamed material having air cells can be cited. As an example of fibers with elasticity, fibers, formed of PE, PP, PET or other thermoplastic material and using such a resin in solitary form or using such resins in a core-sheath structure or side-by-side structure, can be cited.

Preferably, the fibers are those that have been subject to secondary crimping mechanically or by heating, etc. In consideration of fitting comfort, the fiber thickness is preferably adjusted to be in a range from 0.5 dtex to 8.8 dtex and the fiber length is preferably adjusted to be in a range from 3 mm to 64 mm. A laminate of such fibers can be obtained by the method of layering fibers using a card, bonding the fibers by melting the thermoplastic fibers, and thereafter forming by the through air method. A non-woven fabric that is obtained by this method is favorable in having a repulsive elastic property. Besides this, a fabric formed by the generally-used method of point bonding, spun bonding, WJ, or a spun bonding method, wherein a continuous filament is spun and bonded by hot embossing, or an SMS sheet, formed by blowing a melt onto a spun bonded fabric and then performing bonding, etc., may be used. Furthermore, a chemical bonding method, wherein a binder is coated onto the surface after the layering of fibers to perform bonding, or an air laid method may also be used. Meanwhile, as a film with elasticity, a film, obtained by extruding resin such as elastic PE or PP, high elastic urethane, rubber, and such in solitary, composite, or multi-layer form by T-die or inflation method, is used. As a foamed material, a material, obtained by foaming PE or PP, which has elasticity, or foaming urethane, rubber, or other resin of high elasticity, is used. The above-mentioned raw materials may be used in solitary form, be fixed and made into multiple layers by an adhesive agent or embossing, or may be provided with elasticity or rigidity in a fixed direction by embossing.

As another method of providing the elastic sheet with elasticity, the method of providing the elastic sheet with a plurality of microscopic protrusions can be cited. By providing the elastic sheet with a plurality of microscopic protrusions, mutually opposing parts of the elastic sheet at the crease-spanning region are made to curve gradually and prevented from contacting each other and spaces are thus formed between the mutually opposing parts of the elastic sheet. Thus when a pressure is applied from the vestibular floor to the crease-spanning region, the crease-spanning region can expand and deform readily and disperse the pressure in outward directions that intersect the direction of the pressure. Specifically, it is preferable that spaces are formed and parts of the elastic sheet do not contact each other completely within a range of the crease-spanning region with a total length in the lateral direction of not less than 0.5 mm and not more than 40 mm. More preferably, parts of the elastic sheet do not contact each other completely within a range of the crease-spanning region with a total length in the lateral direction of not less than 0.5 mm and not more than 30 mm. Preferably, the plurality of microscopic protrusions are provided within a range of the crease-spanning region with a total length in the lateral direction of not less than 0.5 mm and not more than 40 mm. Furthermore, the height of the microscopic protrusions is preferably in a range from 0.05 mm to 2 mm and the interval of the microscopic protrusions is preferably in a range from, 0.3 mm to 20 mm. For example, a film, having a low-density polyethylene (LDPE) resin as a main component, provided with a plurality of microscopic protrusions, which have a height of 0.2 mm and an interval of 1.5 mm and are positioned in a staggered manner, may be used. As long as such micro-protrusions are equipped, the raw material to be used in the elastic sheet is not limited to the abovementioned elastic raw materials. For example, polyethylene, polypropylene, polyethylene terephthalate, polyvinyl alcohol, polylactic acid, polybutyl succinate, non-woven fabric, paper, laminates of such materials with a thickness of 15 to 60 μm and such, which are raw materials for a water-impermeable sheet, may be used. An air-permeable film, obtained by filling with an inorganic filler and performing a drawing process, may also be used. An open pore film, having a low-density polyethylene (LDPE) resin as the principal component, having open pores of a pore diameter of 0.1 to 0.6 mm at a porosity of 10 to 30%, and being adjusted in basis weight per unit area to within the range from 15 to 35 g/m$^2$ and such, may also be used.

(6) The interlabial pad according to (1), wherein the interlabial pad has a mini sheet piece, with elasticity, attached to the opposite body side face, and wherein the pressure dispersion means is provided in the mini sheet piece.

The interlabial pad according to (6) has a mini sheet piece, which is provided with the pressure dispersion means, equipped at the opposite body side face, and the mini sheet piece, which has elasticity, is attached so as to span the crease. That is, the interlabial pad according to (6) has a mini sheet piece, having the property of deforming and restoring in form readily, provided at the crease spanning region. Thus with the interlabial pad according to (6), when a wearer sits on a chair and such, and the vestibular floor presses the crease-spanning region with a strong pressure, the crease-spanning region, which has the mini sheet piece, can expand and deform readily and disperse the pressure in outward directions that intersect the direction of the pressure. The interlabial pad will therefore hardly press the vestibular floor in repulsion to the pressure and the wearer can go about with daily life comfortably while hardly feeling the sensation of using the interlabial pad. The mini sheet piece may be provided with elasticity by the use of an elastic raw material in the mini sheet piece, and specifically a raw material equivalent to the elastic raw material used in the above-described elastic sheet is used.

(7) The interlabial pad according to (6), wherein entirety of one face of the mini sheet piece is joined to the opposite body side face.

Entirety of one face of the elastic mini sheet piece that is provided so as to span the crease of the interlabial pad according to (7), is joined to the opposite body side face. Since the entirety of one face of the elastic mini sheet is thus put in contact with the crease-spanning region of the interlabial pad, the crease-spanning region can be provided with an adequate elasticity. With the interlabial pad according to (7), which is provided with such a mini sheet piece with elasticity, when a wearer sits on a chair and such, and the vestibular floor presses the crease-spanning region with a strong pressure, the crease-spanning region, which has the mini sheet piece, can expand and deform readily and disperse the pressure in outward directions that intersect the direction of the pressure. The interlabial pad will therefore hardly press the vestibular floor in repulsion to the pressure and the wearer can go about with daily life comfortably while hardly feeling the sensation of using the interlabial pad.

(8) The interlabial pad according to (6), wherein the mini sheet piece is joined to the opposite body side face, which is faced with itself across the crease so that a space is formed between the opposite body side face and the mini sheet piece so as to restrict the separation of the facing opposite body side face from each other in the state of being folded in two.

The mini sheet piece with elasticity, which is provided so as to span the crease of the interlabial pad according to (8) is joined to mutually facing parts of the opposite body side face so as to bridge these parts. Since the mini sheet piece with elasticity thus bridges mutually facing parts of the side face opposite the body side, the respective side parts of the fold are prevented from deforming readily while the crease-spanning region is made readily deformable. With the interlabial pad according to (8), which is provided with such a mini sheet piece with elasticity, when a wearer sits on a chair and such, and the vestibular floor presses the crease-spanning region with a strong pressure, the crease-spanning region, which has the mini sheet piece, can expand and deform readily and disperse the pressure in outward directions that intersect the direction of the pressure. The interlabial pad will therefore hardly press the vestibular floor in repulsion to the pressure and the wearer can go about with daily life comfortably while hardly feeling the sensation of using the interlabial pad. With the interlabial pad according to (8), since a space is formed between the mini sheet piece and the opposite body side face, this space can be used for insertion of a finger. For use for insertion of a finger, the inner circumference of the space that is formed is preferably not less than 40 mm.

(9) The interlabial pad according to any one of (1) to (8), wherein the respective side ends in the longitudinal direction are bent towards the body side face so as to reduce the pressures applied to the interlabial pad when the wearer moves, and wherein flexible lines that serve as axes of the bending are provided at the respective side ends in the longitudinal direction.

Flexible lines are provided at the respective side ends in the longitudinal direction of the interlabial pad according to (9) to enable the respective side ends to bend towards the body side face. In an interlabial pad that is folded in two, since the side end parts in the longitudinal direction of the interlabial pad are not contained in the labia but are exposed in a normal usage state, these parts tend to readily receive pressures due to movements of a wearer in a case where these parts protrude. In regard to this point, with the interlabial pad according to (9), by the bending of the respective side ends in the longitudinal direction towards the body side face, protruding parts are eliminated and the received pressures can be reduced. Thus even if a pressure is applied to the interlabial pad from the exterior, the wearer will hardly be made to feel the sensation of using the interlabial pad. Furthermore, since the respective side end parts in the longitudinal direction are bent towards the body side face, the interlabial pad can be fitted more readily between the labia and the outflow of menstrual blood, the falling-off of the interlabial pad, etc., can be prevented effectively.

As methods of providing the flexible lines, in addition to the method of embossing a continuous or discontinuous line-like emboss pattern on the absorbent, the method of cutting the absorbent with a cutter, etc., to form a continuous or discontinuous line-like pattern, the method of forming regions that differ in rigidity by zoning of materials differing in rigidity in the absorbent, etc., can be cited. Also in order to prevent the outflow of menstrual blood, the falling-off of the interlabial pad, etc., more effectively, the size of the respective side end parts that are bent is set so that the thickness will be in a range preferably from 15 mm to 50 mm and more preferably in a range from 25 mm to 40 mm in consideration of the outer shape of the labia and the distance to the leg openings. Meanwhile the width is preferably in a range from 3 mm to 30 mm and more preferably in a range from 5 mm to 20 mm.

(10) The interlabial pad according to any one of (1) to (9), wherein the interlabial pad is an interlabial pad for urinary incontinence.

The interlabial pad according to (10) can be used as an absorbent pad for urinary incontinence. That is, since the ostium vaginae, from which menstrual blood is discharged, and the urethral meatus, from which urine is discharged, are both positioned between the labia, when the interlabial pad according to (10) is used upon being sandwiched between the labia, it can be used to absorb urine. Since urine can thus be absorbed between the labia and particularly in the vicinity of the urethral meatus by the interlabial pad according to (10), an interlabial pad, which is effective for urinary incontinence, especially urinary incontinence of a light degree, can be provided.

(11) The interlabial pad according to any one of (1) to (9), wherein the interlabial pad is an interlabial pad for absorbing vaginal discharge.

With the interlabial pad according to (11), the interlabial pad can be used for absorbing vaginal discharge. That is, since the interlabial pad according to (11) is used upon being sandwiched between the labia, it can be used to absorb secreted matter (vaginal discharge), besides menstrual blood, from the ostium vaginae and can thus be used for this purpose (for absorbing of vaginal discharge). Since vaginal discharge can thus be absorbed to lighten the discomfort of a wearer by the interlabial pad according to (11), the interlabial pad is also effective for a wearer at times besides during menstruation.

(12) An interlabial pad wrapping body, in which the interlabial pad according to any one of (1) to (11) is enclosed and sealed in an individual wrapping container.

With the interlabial pad wrapping body according to (12), each individual interlabial pad is enclosed and practically sealed in an individual wrapping container, which is filled with air. Thus even when, in a case where a wearer carries the individual wrapping container in a bag, an external pressure is applied to the individual wrapping container, the external pressure can be cushioned by the air. Since an external pressure, which is applied to the crease-spanning region from the side in the direction of the folding in two, can be cushioned in particular, the crease-spanning region will not take on a pointed shape and can be kept in a gradually curving state. Thus with the interlabial pad wrapping body according to (12), since the interlabial pad will not become collapsed even when an external pressure is applied during carrying and the crease-spanning region can be kept in a gradually curving state, an interlabial pad, with which the sensation of use is hardly felt, can be provided.

The volume of the individual wrapping container that is used in the interlabial pad wrapping body according to (12) is at least larger than the volume of the interlabial pad. Specifically, the length of the individual wrapping container is preferably longer than the longitudinal length of the interlabial pad by not more than 80 mm and more preferably longer not less than 40 mm. Also, the width of the individual wrapping container is preferably greater than the lateral length of the interlabial pad by not more than 80 mm and more preferably greater by not more than 40 mm. The thickness of the individual wrapping container is preferably greater than the width of the interlabial pad by not more than 80 mm and more preferably greater by not more than 40 mm. The air filling percentage of the individual wrapping container is preferably in a range from 5 to 60% and more preferably in a range from 10 to 40%. An individual wrapping container having such a size can be formed from a single non-air-permeable sheet. Specifically, the individual wrapping container is formed by wrapping the interlabial pad, which has been folded in two, in the non-air-permeable sheet and providing seal parts that join the non-air-permeable sheet to itself at the regions of overlapping of the non-air-permeable sheet with itself, which are formed by the wrapping process. Of the regions at which the non-air-permeable sheet body overlaps with itself, a tape with adhesive force can be provided at the region that is to be a seal-opening part in order to improve the seal-opening property.

By the present invention, an interlabial pad, with which a wearer will hardly feel the sensation of using the interlabial pad even when the wearer moves and pressure from the exterior is applied to the interlabial pad, can be provided.

DESCRIPTION OF THE PREFERRED EMBODIMENT

Embodiments of the present invention shall now be described with reference to the drawings. With the description of the respective embodiments besides the first embodiment, the description of arrangements, actions, and effects in common to those of the first embodiment shall be omitted.

<First Embodiment>

[Overall Constitution of an Interlabial Pad]

Figure 4:
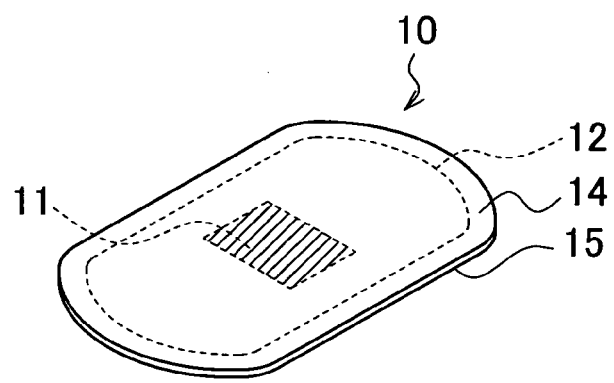
FIG. 4 is a perspective view showing an interlabial pad 10 in the opened state.

FIG. 4 is a perspective view of an interlabial pad 10 of a first embodiment of the present invention in the opened state. As shown in FIG. 4, the interlabial pad 10 of this embodiment has a practically longitudinal shape and thus has a shape with a longitudinal direction and a lateral direction. The interlabial pad 10 has a surface side sheet 14 and a back face side sheet 15, and an absorbent 12 is positioned between the surface side sheet 14 and the back face side sheet 15. The surface side sheet 14 is a liquid-permeable sheet that enables permeation of body fluids of a wearer, and the back face side sheet 15 is a liquid-impermeable sheet that practically does not allow permeation of body fluids of a wearer. At a substantially central portion of the absorbent 12 is provided with a pressure dispersion means 11. Also, the external dimensions of the interlabial pad 10 of this embodiment are set in consideration of the external shape of the labia and the space that is formed between the labia and shorts, and the longitudinal length thereof is approximately 100 mm and the width of each of side parts of the fold at both sides is 30 mm.

Figure 5:
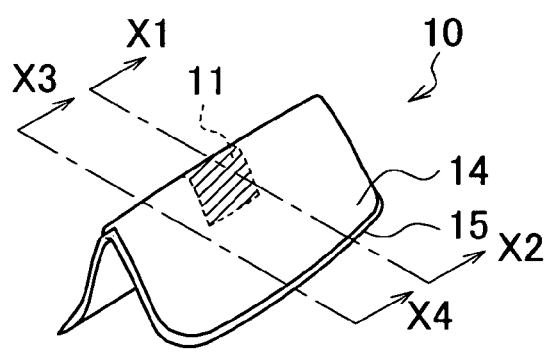
FIG. 5 is a perspective view showing the interlabial pad 10 in the state of being folded in two.

Also as shown in FIG. 5, the interlabial pad 10 of the present embodiment is of a type that is used upon being folded in two along a crease extending in the longitudinal direction so that the back face side sheet 15 faces itself during fitting. This interlabial pad 10, which has been folded in two, has the pressure dispersion means 11 disposed at the absorbent 12 at a region along the crease that extends in the longitudinal direction, and is sandwiched between the labia so that at least a part of the region along the crease contacts the vestibular floor.

[Surface Side Sheet]

As the surface side sheet 14, a liquid-permeable sheet is used, and specifically, a spun-lace non-woven fabric, formed by adjusting fibers, in which natural cotton is mixed at a proportion of not less than 5% and not more than 30% with rayon or acetate of a proportion of not less than 70% and not more than 95%, to have a basis weight per unit area of a range from 20 g/m² to 50 g/m², entangling the fibers by water entanglement, then drying, and adjusting the thickness to be within the range from 0.3 mm to 1.0 mm, is used. In regard to the fiber quality, for the natural cotton, the fiber length is within the range from 15 mm to 60 mm, and for the rayon or acetate, the fiber length is within the range from 25 mm to 51 mm and the fineness is within the range from 1.1 dtex to 6.6 dtex.

[Back Face Side Sheet]

Generally as the back face side sheet, a sheet which can prevent the menstrual blood that is held in the absorbent 12 from leaking out of the interlabial pad 10, can be used. Also, by using a moisture-permeable material, mustiness during fitting can be alleviated and discomfort during fitting can thus be lightened. Specifically as the back face side sheet 15, an air-permeable film, obtained by filling with an inorganic filler and performing a drawing process, or an air-permeable, liquid-blocking sheet, having open pores with a pore diameter in a range from 0.1 to 0.6 mm at a porosity of 10 to 30% and being obtained by positioning capillary tubes so as to be directed towards the absorbent 12, is used. In the case where flexibility that will not lower the fitting comfort is considered, an embodiment using a film, having a low-density polyethylene (LDPE) resin of a density in the range from 0.90 g/cm$^3$ to 0.925 g/cm$^3$ as the main component and having a basis weight in the range from 15 g/m$^2$ to 30 g/m$^2$, can be cited as a modification example.

[Absorbent]

Generally as the absorbent equipped in the interlabial pad, an absorbent, using pulp, chemical pulp, rayon, acetate, natural cotton, polymer absorbent body, fibrous polymer absorbent body, or synthetic fibers in solitary form or using a mixture of the above, may be used. These materials may be used in the form of a sheet or powder. Though there will be no problems as long as the absorbent can absorb and hold body fluids, the absorbent is preferably bulky, lasting in form, and low in chemical irritability to the body. Specifically as the absorbent 12, a non-woven fabric sheet, having a basis weight per unit are of not less than 50 g/m$^2$ and not more than 250 g/m$^2$ and a bulk of not less than 2 mm and not more than 5 mm and being formed by mixing and layering fibers of not more than 60% and not less than 90% rayon or acetate rayon, selected from among those with a fineness in the range from 1.1 dtex to 4.4 dtex, with not less than 10% and not more than 40% fibrous polymer absorbent and forming a sheet by entanglement by needling, is used. Also, in incorporating the absorbent 12 in the interlabial pad 10, changing of the bulk, layering, or overlapping by folding, is performed for adjustment as suited.

[Pressure Dispersion Means]

Figure 6:
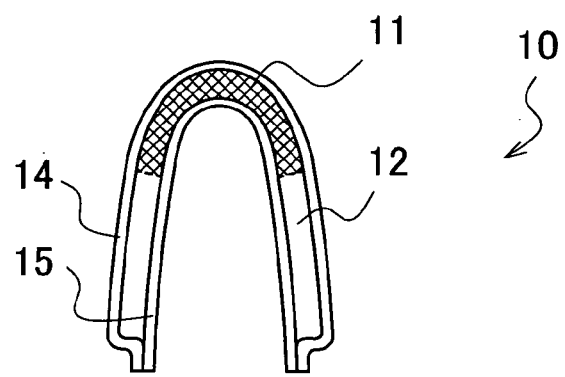
FIG. 6 is a sectional view as sectioned in the X1–X2 direction of the interlabial pad 10 of FIG. 5.
Figure 7:
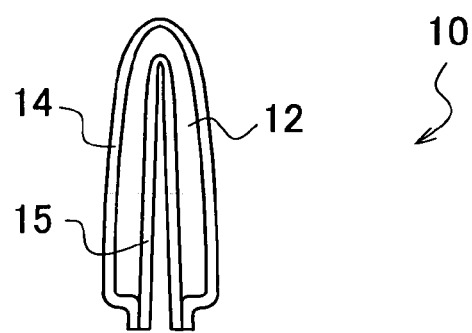
FIG. 7 is a sectional view as sectioned in the X3–X4 direction of the interlabial pad 10 of FIG. 5.

FIG. 6 is a sectional view as sectioned in the X1–X2 direction of the interlabial pad 10 of FIG. 5. FIG. 7 is a sectional view as sectioned in the X3–X4 direction of the interlabial pad 10 of FIG. 5. As shown in these FIGS. 6 and 7, the pressure dispersion means 11 is disposed at a substantially central part of the absorbent 12 so as to span the crease. The pressure dispersion means 11 thus does not have to be provided across the entire range of the absorbent 12 and adequate effects can be provided by providing it just in a narrow region at the substantially central part.

This pressure dispersion means 11 is arranged as a fiber aggregate having fibers that are oriented so as to intersect the crease. Specifically, a non-woven fabric sheet, having a basis weight per unit are of not less than 50 g/m$^2$ and not more than 500 g/m$^2$ and a bulk of not less than 1 mm and not more than 20 mm and being formed by mixing and layering fibers of not more than 60% and not less than 95% rayon or acetate rayon, selected from among those with a fineness in a range from 1.1 dtex to 6.6 dtex, and not less than 5% and not more than 40% natural cotton and forming a sheet by embossing, is used. Also, as modification examples, an arrangement using a sheet, formed by subjecting the abovementioned fibers to the air laid method, melt blown method, spun lacing method, or papermaking method, etc., or a sheet, with which such fibers that have been formed into sheet are subject to embossing of dot-form, lattice-form, etc., as the pressure dispersion means 11 can be cited.

Figure 8:
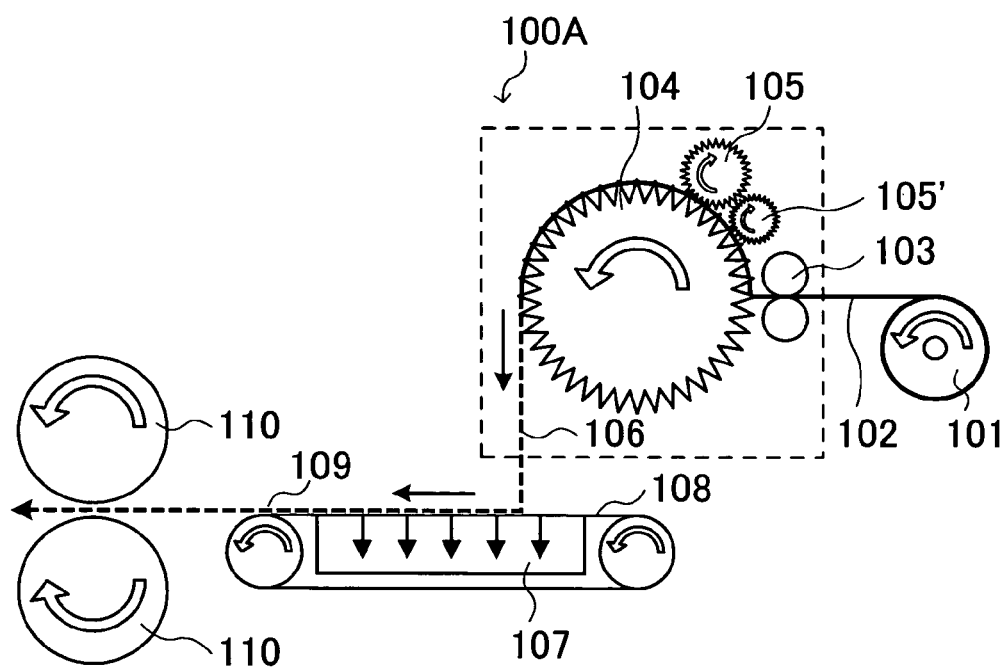
FIG. 8 is a manufacturing process diagram for describing a method of performing fiber opening of a fiber aggregate.

As the method of disposing fibers that are oriented so as to intersect the crease, a method of orienting the fibers randomly is used. A method of randomly orienting fibers of a fiber aggregate of long fiber length shall now be described with reference to FIG. 8. FIG. 8 is a manufacturing process diagram for describing a method of performing fiber opening of a fiber aggregate that forms the pressure dispersion means, and here, a fiber aggregate sheet 102 is conveyed by a pair of rollers 103 from a winding roller 101, around which the fiber aggregate sheet 102 is wound, to a fiber opener 100A. This fiber opener 100A has a garnet type fiber opening roller 104, with which wave-like blades are aligned in a plurality of threads, and fiber opening is performed by passage through this fiber opening roller 104. In order to improve the fiber opening property in this process, it is preferable to pass the fiber aggregate sheet through combination of a plurality of small cutter rollers 105 and 105', which are disposed in a staggered manner so that the edges of adjacent wave-like blades that are aligned in a plurality of threads alternate with respect to each other and are made to rotate in the opposite direction of the rotation direction of the fiber opening roller 104. This fiber opening method is not restricted to the use of a garnet type arrangement and a hammer mill arrangement, etc., may be used instead.

Fibers 106, which have thus been opened, are drawn by suction by a suction device 107, disposed at the inner side of a mesh-like conveyor belt 108 and the fibers 106 are thereby layered as an aggregate on the conveyor belt 108. In this process, at the same time as the separation of the fibers from the wave-like blades of the fiber opening roller 104, the opened fibers 106 are subject to the suction speed due to the suction. Since when the suction pressure is in a range from 1500 to 15000 Pa, a capture speed of not less than 4 m/sec and not more than 200 m/sec (the range from 240 m/min to 1200 m/min) is applied to the opened fibers 106, the capture speed that is applied to the opened fibers 106 will be higher relative to the conveying speed of the range from 20 m/min to 200 m/min of the conveyor belt 108 and it becomes difficult for the fiber orientation to be directed in the MD direction. Here, the MD direction is the direction of progress of the conveyor belt 108, that is, the direction of progress of the fiber aggregate 109.

The fiber orientation of the fiber aggregate 109 of long fiber length can thus be made random in the process of layering the opened fibers 106 on the conveyor belt in the manufacturing process by making the capture speed, which is applied to the fibers 106 from the point immediately after opening, high relative to the conveying speed of the conveyor belt 108. The capture speed applied to the opened fibers 106 is mainly determined by the suction force of the suction device 107, disposed at the inner side of the mesh-like conveyer belt 108. The capture speed applied to the fibers can be made high relative to the conveyor speed of the conveyor belt by selecting the suction pressure, to be applied across the layered fiber aggregate 109 and the mesh-like conveyor belt, to be within the range from 1500 Pa to 15000 Pa when the conveying speed is not less than 20 m/min and not more than 200 m/min. A suction pressure of less than 1500 Pa is not preferable in that, depending on the conveying speed, the fibers will tend to orient readily towards the MD, and a suction pressure of more than 15000 Pa is not preferable in that the fibers 106 become entangled excessively with the mesh of the conveyor belt, making it difficult to transfer the fiber aggregate 109 to a subsequent process.

[Action(s) and Effect(s)]

Figure 1:
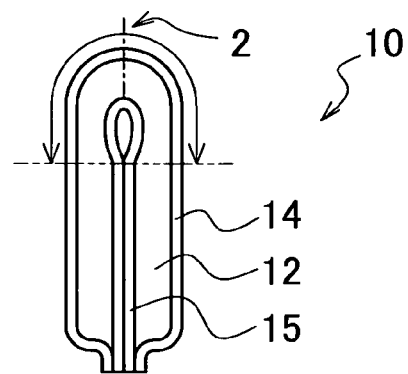
FIG. 1 is a sectional view as sectioned in the lateral direction of an interlabial pad 10 a first embodiment of the present invention in the fitted state.
Figure 2:
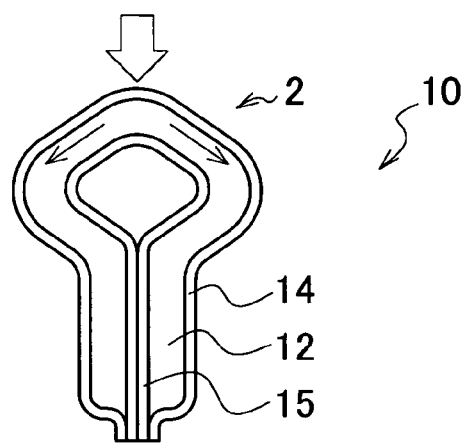
FIG. 2 is a drawing for describing the circumstances when a pressure is applied to a crease-spanning region of the interlabial pad 10.
Figure 3:
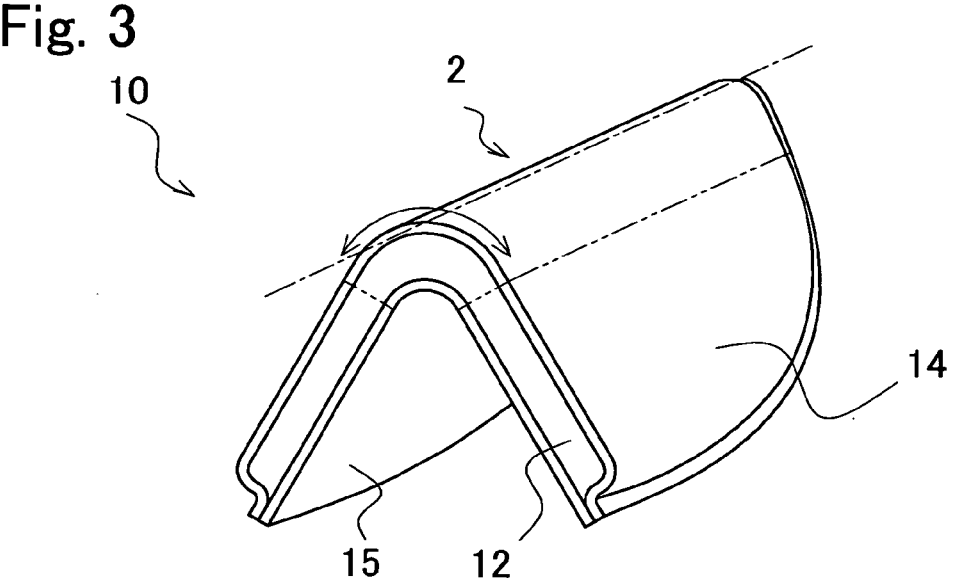
FIG. 3 is a sectional perspective view as sectioned in the lateral direction of the interlabial pad 10.

With the interlabial pad 10 of the first embodiment, since the pressure dispersion means 11 is provided at the absorbent 12 so as to span the crease, when the vestibular floor presses the crease-spanning region 2 from above with a strong pressure in accompaniment to a wearer sitting on a chair, etc., the crease-spanning region 2, which has repulsive rigidity, can expand and deform readily and disperse the pressure in outward directions that intersect the direction of the pressure as shown in FIGS. 1 and 2. The interlabial pad 10 will therefore hardly press the vestibular floor in repulsion to the pressure and the wearer can go about with daily life comfortably while hardly feeling the sensation of using the interlabial pad.

Modification Example 1

Figure 9:
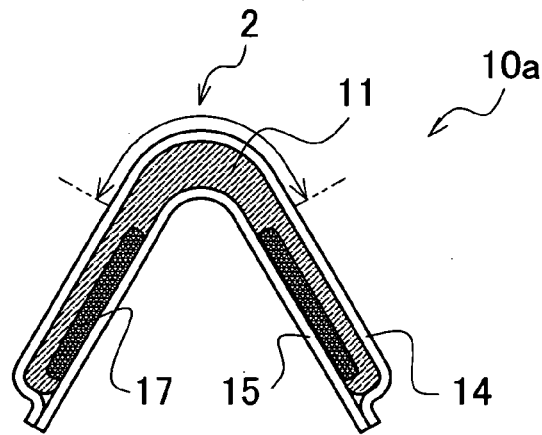
FIG. 9 is a sectional view as sectioned in the lateral direction of an interlabial pad 10a of a Modification Example 1 of the first embodiment in the folded-in-two state.

A Modification Example 1 of the first embodiment is characterized in that a rigid raw material 17 is used in a part of the absorbent 12 which does not span the crease of the interlabial pad 10 of the first embodiment. FIG. 9 is a sectional view as sectioned in the lateral direction of the interlabial pad 10a of the Modification Example 1 of the first embodiment in the folded-in-two state. Specifically, pulp of a fiber length of not more than 8 mm, which has been layered to a basis weight per unit area of 100 g/m², is used as the rigid raw material 17 at the parts of the absorbent 12 at the regions not spanning the crease, and as the pressure dispersion means 11, a mixture of 85% rayon of a fiber length of 51 mm and fineness of 3.3 dtex with 15% natural cotton is layered to a basis weight per unit area of 180 g/m² with the fibers being oriented so as to intersect the crease. The crease in this Modification Example 1 lies along the longitudinal central line and the crease-spanning region 2 is in a range of within 5 mm in the lateral directions of the longitudinal central line, that is, in a range of within 10 mm spanning the longitudinal central line. Furthermore, the absorbent 12 is embossed to an embossed area percentage of 1.8% by a dot-form emboss pattern. With this interlabial pad 10a of the Modification Example 1, since when the vestibular floor contacts the crease-spanning region 2 with a strong pressure, the regions which do not span the crease and have the rigid raw material 17, do not deform readily, and the crease-spanning region 2 expands and deforms even more readily so that a strong repulsive force is not applied to the vestibular floor and a wearer will hardly feel the sensation of use. Embodiments may also be employed, where, in place of using the rigid raw material 17, the absorbent 12 is increased in basis weight per unit area or increased in density or is provided with rigidity by the addition of an adhesive agent.

Modification Example 2

With a Modification Example 2 of the first embodiment, slitting is applied as the pressure dispersion means 11 that is provided in the interlabial pad 10 of the first embodiment. Specifically, the slits have a dimension within a range from 1 mm to 20 mm, are of a pitch in a range of not more than 20 mm, and form an intersecting slit pattern. The shape of the slits is linear and these slits pass through in the thickness direction. With this Modification Example 2 of the first embodiment, effects that are equivalent to the effects of the first embodiment can be obtained.

Modification Example 3

With a Modification Example 3 of the first embodiment, embossing is applied as the pressure dispersion means 11 provided in the interlabial pad 10 of the first embodiment. Specifically, a plurality of dot-form embosses are formed at a pitch in a range from 5 mm to 20 mm in the crease-spanning region. With this Modification Example 3 of the first embodiment, effects that are equivalent to the effects of the first embodiment can be obtained.

Modification Example 4

With a Modification Example 4 of the first embodiment, the pressure dispersion means 1.1 is provided in the surface side sheet 14 in the crease-spanning region 2 of the interlabial pad 10 of the first embodiment. The pressure dispersion means 11 of this Modification Example 4 is arranged from a fiber aggregate having fibers that are oriented so as to intersect the crease. Specifically, a fiber aggregate, with which the fibers used in the surface side sheet 14 are oriented so as to intersect the crease, is used as the pressure dispersion means 11. As in this Modification Example 4, effects equivalent to those of the first embodiment can be obtained by providing the pressure dispersion means 11 in the surface side sheet.

<Second Embodiment>

Figure 10:
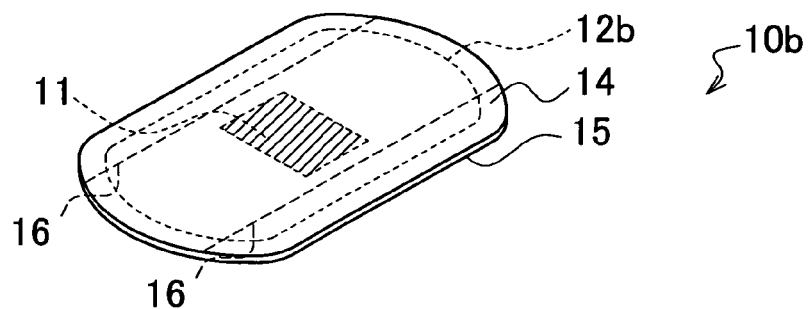
FIG. 10 is a perspective view showing an interlabial pad 10b of a second embodiment in the opened state.
Figure 12:
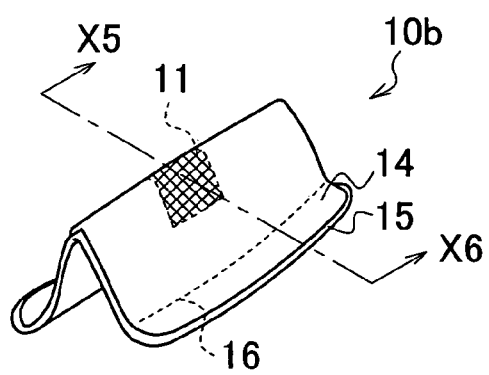
FIG. 12 is a perspective view showing the interlabial pad 10b in the state of being folded in two.

FIG. 10 is a perspective view of an interlabial pad 10b of a second embodiment. As shown in this FIG. 10, with the interlabial pad 10b of the second embodiment, the interlabial pad 10 of the first embodiment is provided with flexible lines 16 at both side ends in the longitudinal direction. Thus as shown in FIG. 12, this interlabial pad 10b has a structure, wherein, upon being folded in two, the interlabial pad is sandwiched between the labia in the state in which both side ends in the longitudinal direction are bent towards the body side face with the flexible lines 16 as the bending axes.

[Flexible Line]

Figure 11:
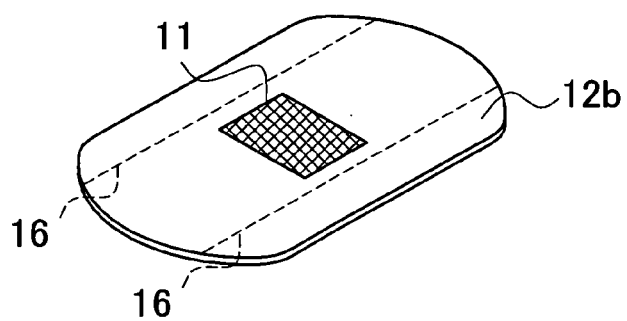
FIG. 11 is a perspective view of an absorbent 12b of the interlabial pad 10b

FIG. 11 is a perspective view of an absorbent 12b of the interlabial pad 10b of the second embodiment. As shown in FIG. 11, the flexible lines 16 are disposed at the respective side ends of the absorbent 12b, and more specifically, are disposed substantially parallel to the longitudinal central line of the absorbent 12b at positions separated from the respective side edges of the absorbent 12b by approximately 10 mm. The flexible lines 16 are formed by applying embossing of a continuous, line-like pattern to the respective side ends of the absorbent 12b.

[Action(s) and Effect(s)]

Figure 13:
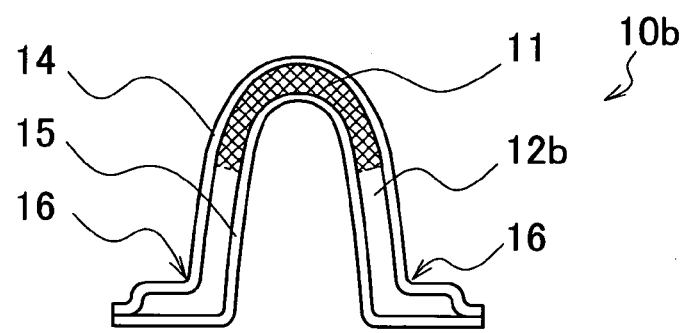
FIG. 13 is a sectional view as sectioned in the X5–X6 direction of the interlabial pad 10b of FIG. 12.

FIG. 13 is a sectional view as sectioned in the X5–X6 direction of the interlabial pad 10b of FIG. 12. As shown in FIG. 13, with the interlabial pad 10b, the same effects as those of the first embodiment can be obtained since the pressure dispersion means 11 is provided so as to span the crease. In addition, since both side ends in the longitudinal direction are bent towards the body side face and the side ends of the interlabial pad do not protrude towards the opposite body side, pressures that the interlabial pad 10b receive when a wearer moves can be reduced. Since the interlabial pad 10b can thus disperse pressures received from the vestibular floor when a wearer moves and the interlabial pad 10b has a structure that does not tend to receive pressures from the vestibular floor to start with, the wearer will hardly feel the sensation of use. Also, the shape is one that fits more readily between the labia and the outflow of menstrual blood, the falling-off of the interlabial pad 10b, etc., can also be prevented effectively.

<Third Embodiment>

Figure 14:
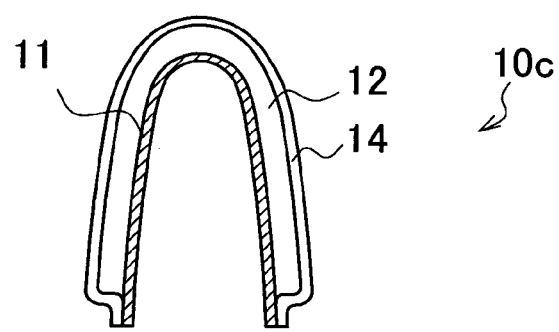
FIG. 14 is a sectional view as sectioned in the lateral direction of an interlabial pad 10c of a third embodiment in the folded-in-two state.

With the interlabial pad 10 of the first embodiment and the interlabial pad 10b of the second embodiment, the pressure dispersion means 11 is disposed at the absorbent 12 and the absorbent 12b, respectively. Meanwhile, in an interlabial pad 10c of a third embodiment, the pressure dispersion means 11 is disposed not at the absorbent 12 but at an elastic sheet that is equipped at the opposite body side face. FIG. 14 is a sectional view as sectioned in the lateral direction of the interlabial pad 10c of the third embodiment in the folded-in-two state. As shown in FIG. 14, with the interlabial pad 10c, an elastic sheet is provided across the entire surface of the opposite body side face, and the same effects as those of the first embodiment can be obtained. Since it is sufficient that the elastic sheet be disposed only in the crease-spanning region, an embodiment may also be employed wherein the elastic sheet is disposed only in the crease-spanning region.

The elastic sheet uses fibers, which are formed of PE, PP, PET or other thermoplastic material and are formed by using such a resin in solitary form or using such resins in a core-sheath structure or side-by-side structure and then subjecting the fibers to secondary crimping. The fiber thickness is adjusted to be in a range from 0.5 dtex to 8.8 dtex and the fiber length is adjusted to be in a range from 3 mm to 64 mm. These fibers are layered, bonded by the melting of the thermoplastic fibers, and formed into the elastic sheet by the method of forming by the through air method.

Modification Example 1

Figure 15:
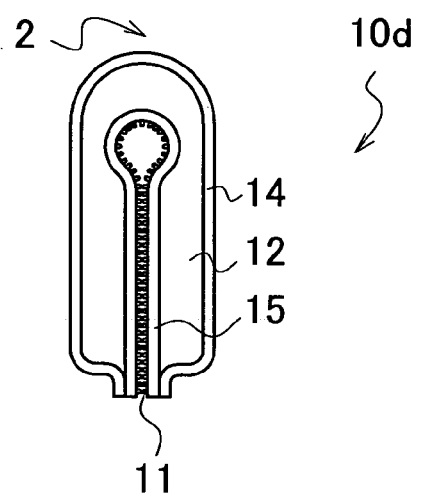
FIG. 15 is a sectional view as sectioned in the lateral direction of an interlabial pad 10d of a Modification Example 1 of the third embodiment in the folded-in-two state.

An interlabial pad 10d of a Modification Example 1 of the third embodiment has an elastic sheet, provided with a plurality of microscopic protrusions, equipped as the pressure dispersion means 11 at the opposite body side face in the crease-spanning region. FIG. 15 is a sectional view as sectioned in the lateral direction of the interlabial pad 10d of the Modification Example 1 of the third embodiment in the folded-in-two state. Though with this Modification Example 1, the protrusions are disposed across the entirety of the opposite body side face, it is sufficient that the protrusions be disposed within a total lateral length range from 0.5 mm to 30 mm in the crease-spanning range. The microscopic protrusions have a height of 0.2 mm and an interval of 1.5 mm, and a film, formed of low-density polyethylene (LDPE) resin as the principal component and having the microscopic protrusions positioned in staggered manner, is used. Effects equivalent to the effects of the first embodiment can thus also be obtained by the Modification Example 1 of the third embodiment, which has the elastic sheet, provided with the plurality of microscopic protrusions, as the pressure dispersion means 11.

<Fourth Embodiment>

Figure 16:
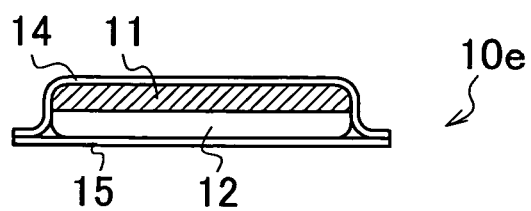
FIG. 16 is a sectional view as sectioned in the lateral direction of an interlabial pad 10e of a fourth embodiment in the opened state.
Figure 17:
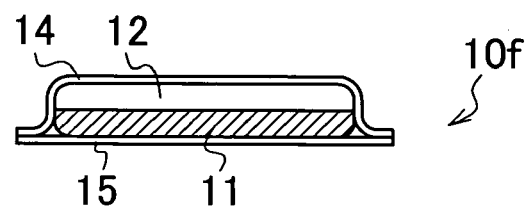
FIG. 17 is a sectional view as sectioned in the lateral direction of an interlabial pad 10f of a Modification Example 1 of the fourth embodiment in the opened state.
Figure 18:
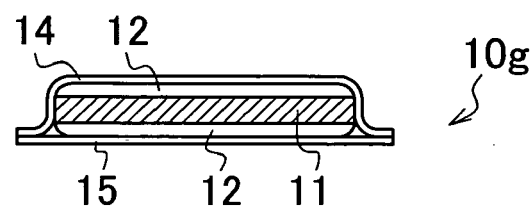
FIG. 18 is a sectional view as sectioned in the lateral direction of an interlabial pad 10g of a Modification Example 2 of the fourth embodiment in the opened state.

FIG. 16 is a sectional view as sectioned in the lateral direction of an interlabial pad 10e of a fourth embodiment in the opened state. As shown in FIG. 16, the interlabial pad 10e of the fourth embodiment has a sheet member with elasticity positioned as the pressure dispersion means 11 between the absorbent 12 and the surface side sheet 14. Also as modification examples with which the position of the pressure dispersion means 11 is changed, an interlabial pad 10f (Modification Example 1), with which the pressure dispersion means is positioned between the back face side sheet 15 and the absorbent 12, and an interlabial pad 10g (Modification Example 2), with which the pressure dispersion means is positioned in sandwiched form in the absorbent 12, can be cited. The interlabial pad 10f of the Modification Example 1 and the interlabial pad 10g of the Modification Example 2 are shown in the opened state in sectional views as sectioned in the lateral direction in FIGS. 17 and 18. As the sheet member with elasticity, a non-woven fabric using an elastic raw material is used. More specifically, a non-woven fabric, obtained by layering PE fibers with elasticity, bonding the fibers by melting the thermoplastic fibers, and thereafter forming by the through air method, is used. Effects equivalent to the effects of the first embodiment can thus be obtained by such a type equipped with a sheet member with elasticity as well.

<Fifth Embodiment>

Figure 19:
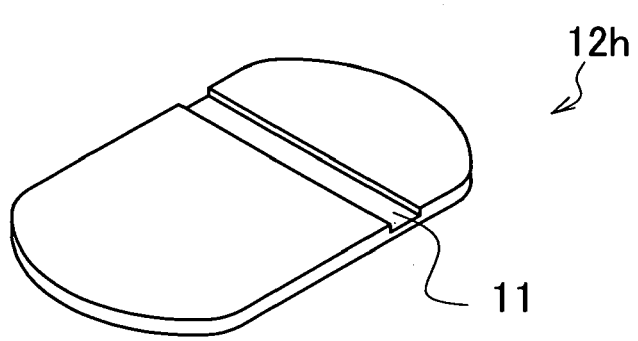
FIG. 19 is a perspective view of an absorbent 12h of an interlabial pad 10h of a fifth embodiment.

FIG. 19 is a perspective view of an absorbent 12h of an interlabial pad 10h of a fifth embodiment. As shown in FIG. 19, the absorbent 12h of the interlabial pad 10h of this fifth embodiment has embossing applied as the pressure dispersion means 11 at the crease-spanning region. This embossing is applied along a straight line and substantially parallel to the lateral central line of the absorbent 12h so as to span the crease. As the embossing, flat pattern embossing is performed by passing the absorbent between two rolls provided with a flat emboss pattern. Effects equivalent to the effects of the first embodiment can thus be obtained by the fifth embodiment to which embossing is applied.

<Sixth Embodiment>

Figure 20:
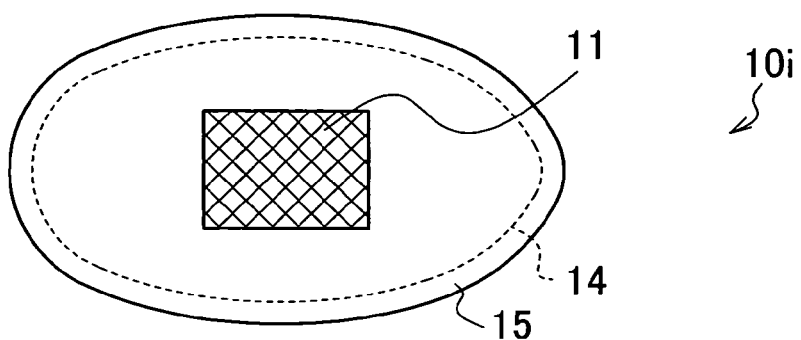
FIG. 20 is a plan view as viewed from the side of the side face opposite the body side of an interlabial pad 10i of a sixth embodiment in the opened state.
Figure 21:
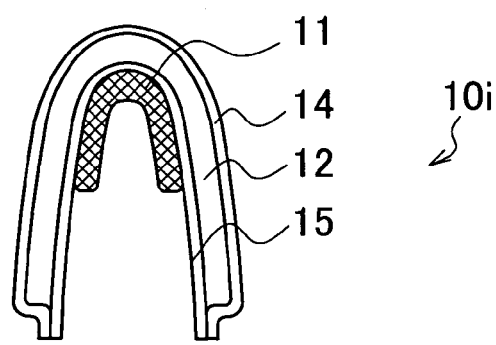
FIG. 21 is a sectional view as sectioned in the lateral direction of the interlabial pad 10i in the folded-in-two state.

FIG. 20 is a plan view as viewed from the opposite body side of an interlabial pad 10i of a sixth embodiment in the opened state. A mini sheet piece is provided as the pressure dispersion means 11 at a substantially central portion of the interlabial pad 10i. This mini sheet piece has one face joined across its entirety to the back face side sheet 15 and is joined to the back face side sheet so as to span the crease when the interlabial pad is folded in two. FIG. 21 is a sectional view as sectioned in the lateral direction of the interlabial pad 10i in the folded-in-two state. The mini sheet piece has elasticity and uses a non-woven fabric using an elastic raw material. More specifically, a non-woven fabric, obtained by layering PE fibers with elasticity, bonding the fibers by melting the thermoplastic fibers, and thereafter forming by the through air method, is used. Effects equivalent to the effects of the first embodiment can thus be obtained by the interlabial pad 10i of the sixth embodiment, with which a mini sheet piece is attached to the opposite body side face at the crease-spanning region.

Modification Example 1 and Modification Example 2

Figure 22:
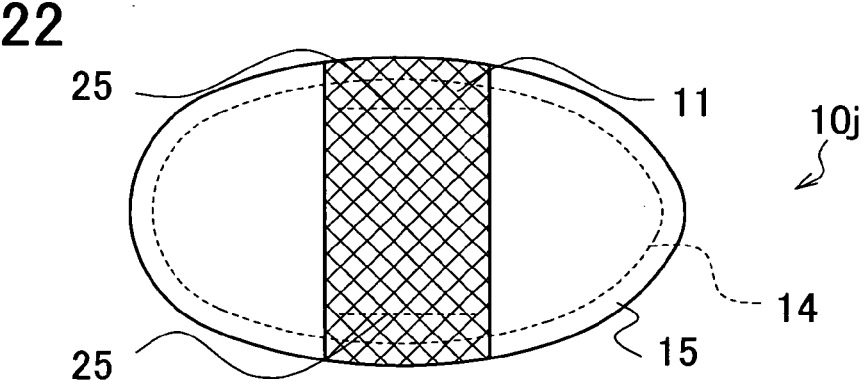
FIG. 22 is a plan view as viewed from the side face opposite the body side of an interlabial pad 10j of a Modification Example 1 of the sixth embodiment in the folded-in-two state.
Figure 23:
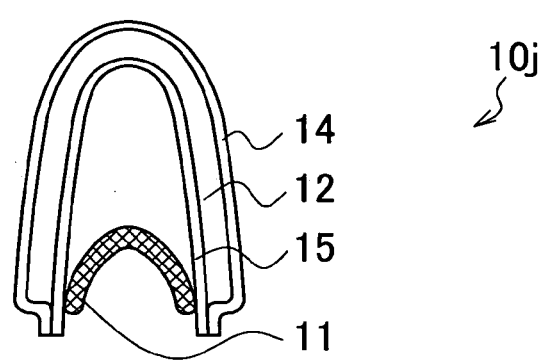
FIG. 23 is a sectional view as sectioned in the lateral direction of the interlabial pad 10j of the Modification Example 1 of the sixth embodiment in the folded-in-two state.
Figure 24:
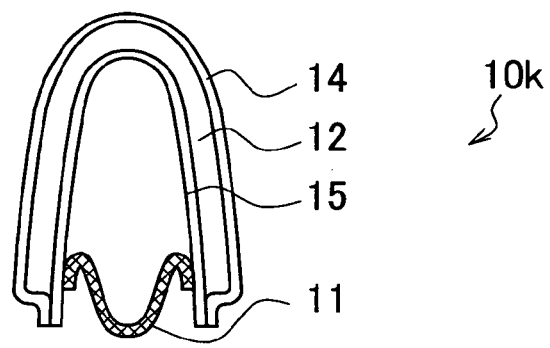
FIG. 24 is a sectional view as sectioned in the lateral direction of an interlabial pad 10k of a Modification Example 2 of the sixth embodiment in the folded-in-two state.

FIG. 22 is a plan view as viewed from the opposite body side face of an interlabial pad 10j of a Modification Example 1 of the sixth embodiment in the folded-in-two state. As shown in FIG. 22, with this Modification Example 1, the mini sheet piece is joined to portions of the opposite body side face that faces each other across the crease so that a space is formed between the mini sheet piece and the opposite body side face. FIG. 23 is a sectional view as sectioned in the lateral direction of this interlabial pad 10j in the folded-in-two state. As shown in FIG. 23, the mini sheet piece of the interlabial pad 10j of the Modification Example 1 is formed to a substantially reversed-V-like shape in FIG. 23. Meanwhile, in an interlabial pad 10k of a Modification Example 2, the mini sheet piece is formed to a substantially reversed-W-like shape, and FIG. 24 is a sectional view as sectioned in the lateral direction of the interlabial pad 10k of this Modification Example 2 in the folded-in-two state. With the interlabial pad 10j of the Modification Example 1 and the interlabial pad 10k of the Modification Example 2, in each of which a mini sheet is provided, the same effects as those of the first embodiment can be obtained. Also, the space that is formed between the mini sheet piece and the opposite body side face can be used as a finger insertion space, into which a finger of a wearer is inserted. Each of the interlabial pads 10j and 10k is manufactured by joining the mini sheet piece to mutually facing portions of the opposite body side face after folding the interlabial pad in two.

Modification Example 3

Figure 25:
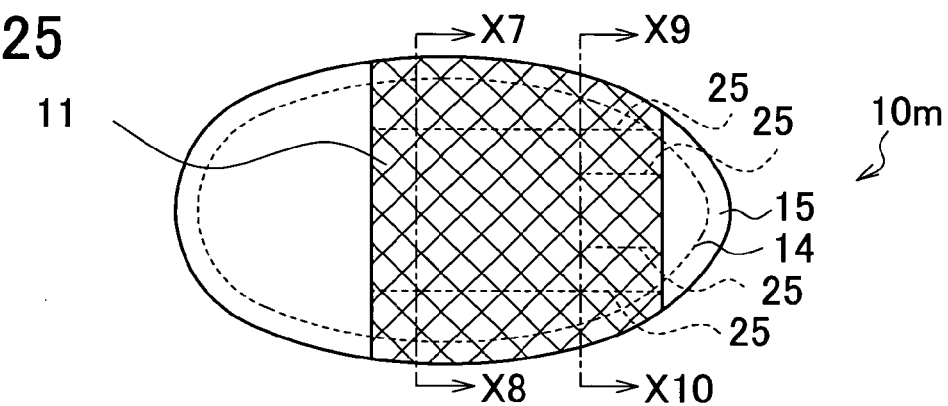
FIG. 25 is a plan view as viewed from the side face opposite the body side of an interlabial pad 10m of a Modification Example 3 of the sixth embodiment in the folded-in-two state.
Figure 26:
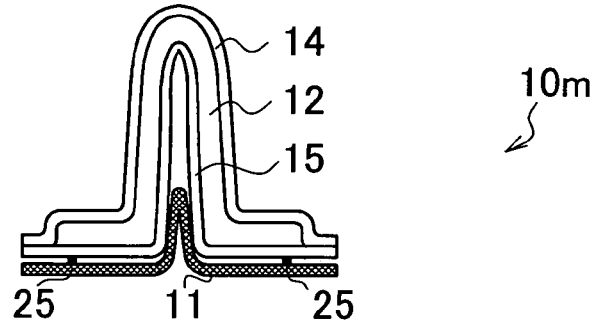
FIG. 26 is a sectional view as sectioned in the X9–X10 direction of the interlabial pad 10m of FIG. 25.
Figure 27:
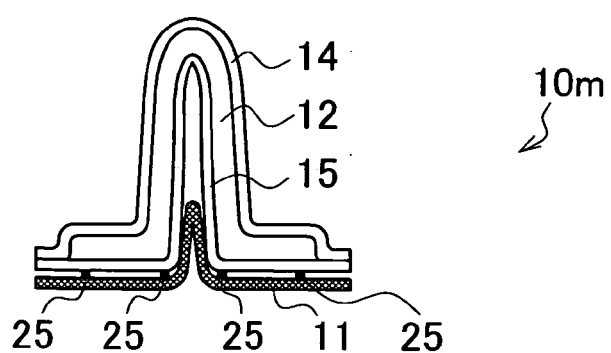
FIG. 27 is a sectional view as sectioned in the X7–X8 direction of the interlabial pad 10m of FIG. 25.

FIG. 25 is a plan view as viewed from the opposite body side face of an interlabial pad 10m of a Modification Example 3 of the sixth embodiment in the folded-in-two state. With this interlabial pad 10m, the mini sheet piece is provided so as to span from one side edge to the other side edge in the longitudinal direction and so as to be biased towards one side in the longitudinal direction. Also, this mini sheet piece is joined at both side ends in the longitudinal direction to the opposite body side face and is also joined to the opposite body side face at an end part at the one side in the longitudinal direction towards which it is biased. FIG. 26 is a sectional view as sectioned in the X7–X8 direction of the interlabial pad 10m of FIG. 25 and FIG. 27 is a sectional view as sectioned in the X9–X10 direction of the same. Thus with the interlabial pad 10m of the Modification Example 3, the opposite body side face is covered over a wide range by the mini sheet piece and since a structure that does not receive pressures from the exterior to start with is thus provided, the effects of the first embodiment can be exhibited more effectively. Also, the space that is formed between the mini sheet piece and the opposite body side face can be used as a finger insertion space, into which a finger of a wearer is inserted, and since the end part at one side is joined to the opposite body side face, a pocket-like structure is arranged. Since the insertion of a finger is thus restricted within a fixed range, the problem of damaging the interior of the labia by a finger in the fitting process can be avoided.

<Interlabial Pad Wrapping Body 30>

Figure 28:
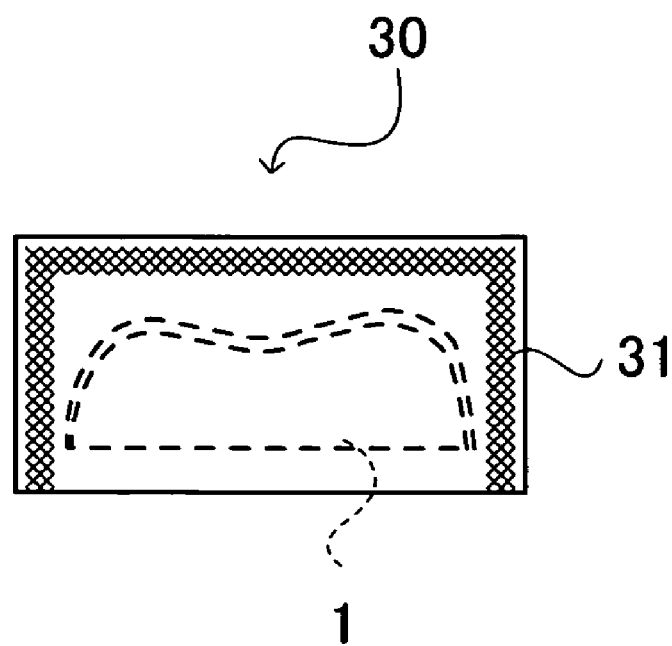
FIG. 28 is a plan view of an interlabial pad wrapping body 30, in which the interlabial pad 1 is enclosed and sealed in an individual wrapping container.

FIG. 28 is a plan view of an interlabial pad wrapping body 30, in which the interlabial pad 1 is enclosed and sealed in an individual wrapping container. This interlabial pad wrapping body 30 is formed by wrapping the interlabial pad 1 in a single non-air-permeable sheet and providing seals 31 that join the non-air-permeable sheet to itself at the regions of overlapping of the non-air-permeable sheet with itself, which are formed by the wrapping process. More specifically, the interlabial pad 1 is contained inside the interlabial pad wrapping body 30 in the state of being folded in two at the crease, and in this state, the interlabial pad 1 has a longitudinal length of 110 mm, a lateral length of 35 mm, and a thickness of 7 mm, and the interlabial pad wrapping body 30 has a longitudinal length of 135 mm, a lateral length of 35 mm, and a thickness of 8 mm. The air filling percentage is 30%. With such an interlabial pad wrapping body 30, since collapsing of the interlabial pad will not occur even when an external pressure is applied during carrying, and the crease-spanning region 2 can be kept in the gradually curved state, the interlabial pad 1, with which a wearer will hardly feel the sensation of use, can be provided.

What is claimed is:

1. An interlabial pad, comprising, in a fitted state:
a body side face facing a body side; and
an opposite body side face facing a side opposite to the body side face, and being formed to a longitudinal shape having a longitudinal direction and a lateral direction;
wherein the interlabial pad is fitted by being folded in two so that the opposite body side face faces itself in the lateral direction, and is held between the labia such that at least a part of a portion along a crease contacts a vestibular floor in the labia, the crease being formed by folding the interlabial pad along a folding axis,
wherein the interlabial pad is equipped, at a crease-spanning region spanning the crease, with a pressure dispersion means which, in response to a pressure that is applied to the interlabial pad when a wearer moves, prevents the pressure from being directly transmitted to the vestibular floor,
wherein the interlabial pad has a fiber aggregate equipped at the crease-spanning region,
wherein the pressure dispersion means has fibers oriented so as to cross the crease in order to control a repulsion against the pressure,
wherein the pressure dispersion means exhibits a ratio of a maximum tensile strength in a machine direction of the fiber aggregate to a maximum tensile strength in a crosswise direction of the fiber aggregate that is between 0.5 and 2.5,
wherein the pressure dispersion means has a Young's modulus which is between 300 kg/mm$^2$ and 1000 kg/mm$^2$, and
wherein the pressure dispersion means has a fineness which is between 1.1 detex and 6.6 detex.

2. The interlabial pad according to claim 1, wherein flexible lines that serve as bending axes are provided at sides parallel to the longitudinal direction of the interlabial pad in order to bend toward the body side face to reduce the pressure applied to the interlabial pad when the wearer moves.

3. An interlabial pad, comprising, in a fitted state:
a body side face facing a body side; and
an opposite body side face facing a side opposite to the body side face, and being formed to a longitudinal shape having a longitudinal direction and a lateral direction;
wherein the interlabial pad is fitted by being folded in two so that the opposite body side face faces itself in the lateral direction, and is held between the labia such that at least a part of a portion along a crease contacts a vestibular floor in the labia, the crease being formed by folding the interlabial pad along a folding axis,
wherein the interlabial pad is equipped, at a crease-spanning region spanning the crease, with a pressure dispersion means which, in response to a pressure that is applied to the interlabial pad when a wearer moves, prevents the pressure from being directly transmitted to the vestibular floor,
wherein the interlabial pad has a fiber aggregate equipped at the crease spanning region,
wherein the pressure dispersion means has fibers oriented so as to cross the crease in order to control a repulsion against the pressure,
wherein the pressure dispersion means exhibits a ratio of a maximum tensile strength in a machine direction of the fiber aggregate to a maximum tensile strength in a crosswise direction of the fiber aggregate that is between 0.5 and 2.5,
wherein the pressure dispersion means has a Young's modulus which is between 300 kg/mm$^2$ and 1000 kg/mm$^2$,
wherein the pressure dispersion means has a fineness which is between 1.1 detex and 6.6 detex, and
wherein the interlabial pad is an interlabial pad for urinary incontinence.

4. An interlabial pad, comprising, in a fitted state:
a body side face facing a body side; and
an opposite body side face facing a side opposite to the body side face, and being formed to a longitudinal shape having a longitudinal direction and a lateral direction;

wherein the interlabial pad is fitted by being folded in two so that the opposite body side face faces itself in the lateral direction, and is held between the labia such that at least a part of a portion along a crease contacts a vestibular floor in the labia, the crease being formed by folding the interlabial pad along a folding axis, wherein the interlabial pad is equipped, at a crease-spanning region spanning the crease, with a pressure dispersion means which, in response to a pressure that is applied to the interlabial pad when a wearer moves, prevents the pressure from being directly transmitted to the vestibular floor, wherein the interlabial pad has a fiber aggregate equipped at the crease spanning region, wherein the pressure dispersion means has fibers oriented so as to cross the crease in order to control a repulsion against the pressure, wherein the pressure dispersion means exhibits a ratio of a maximum tensile strength in a machine direction of the fiber aggregate to a maximum tensile strength in a crosswise direction of the fiber aggregate that is between 0.5 and 2.5, wherein the pressure dispersion means has a Young's modulus which is between 300 kg/mm$^2$ and 1000 kg/mm$^2$, wherein the pressure dispersion means has a fineness which is between 1.1 detex and 6.6 detex, and wherein the interlabial pad is an interlabial pad for absorbing vaginal discharge.

5. An interlabial pad wrapping body, in which the interlabial pad according to claim 1 is enclosed and sealed in an individual wrapping container.

* * * * *